United States Patent [19]

Reusser

[11] 4,362,817
[45] Dec. 7, 1982

[54] HYBRID PLASMID AND PROCESS OF MAKING SAME

[75] Inventor: Fritz Reusser, Portage, Mich.

[73] Assignee: The Upjohn Company, Kalamazoo, Mich.

[21] Appl. No.: 239,258

[22] Filed: Mar. 2, 1981

[51] Int. Cl.³ ............... C12N 15/00; C12N 1/20; C12N 1/00; C12R 1/19
[52] U.S. Cl. ................... 435/172; 435/253; 435/317; 435/849
[58] Field of Search ............ 435/172, 317, 253, 906, 435/849

[56] References Cited

PUBLICATIONS

Science, vol. 196, Apr., 1977–editorial.
Sutcliff, J. G., *Nucleic Acids Research* 5, 2721–2728, 1978.
Chakrabartz, Genetic Engineering CRC Press Inc. pp. 83 to 111 (1978).
Bolivar et al., Gene, vol. 2, pp. 95 to 113 (1977).
Sokaguchi et al., Molecular Breeding and Genetics of Microorganisms Academic Press Inc., pp. 130 to 137 (1980).
Francis et al., Con. J. Microbiol vol. 21, pp. 911 to 919 (1975).

*Primary Examiner*—Alvin E. Tanenholtz
*Attorney, Agent, or Firm*—Roman Saliwanchik

[57] ABSTRACT

A novel chemical compound, plasmid pUC1060, which was constructed from Streptomyces sp. 3022a chromosomal DNA and plasmid pBR322. Hybrid plasmid pUC1060 contains a functional tet gene promoter composed of streptomycete and *E. coli* DNA, and, thus, is useful as a cloning vehicle in recombinant DNA work. For example, using well known DNA methodology, a desired gene, for example, the insulin gene, can be inserted into pUC1060 and the resulting plasmid can then be transformed into a suitable host microbe which, upon culturing, produces the desired insulin.

6 Claims, 1 Drawing Figure

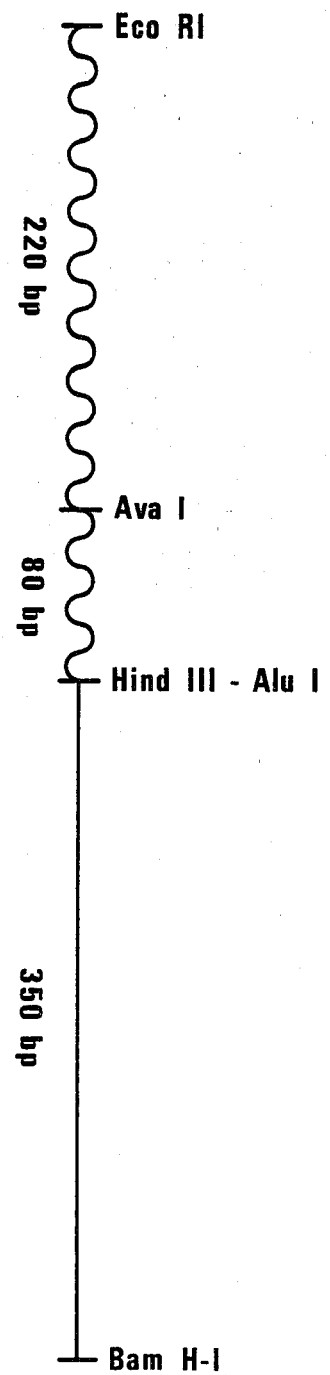

HYBRID PLASMID AND PROCESS OF MAKING SAME

DESCRIPTION

BACKGROUND OF THE INVENTION

The development of plasmid vectors useful for recombinant DNA genetics among microorganisms is well known. The editorial in Science, Vol. 196, April, 1977, gives a good summary of DNA research. This editorial is accompanied by a number of supporting papers in the same issue of Science.

Plasmid pBR322 is a well known plasmid which can be obtained from *E. coli* RR1, NRRL B-12014. The restriction endonuclease map for pBR322 is published; Sutcliff, J. G. "pBR322 restriction map derived from the DNA sequence: accurate DNA size markers up to 4361 nucleotide pairs long." Nucleic Acids Research 5, 2721–2728, 1978. This map is incorporated herein by reference to the above publication.

BRIEF SUMMARY OF THE INVENTION

Plasmid pUC1060 is constructed from *Streptomyces* sp. 3022a, NRRL B-11441 chromosomal DNA and plasmid pBR322. Thus, hybrid plasmid pUC1060 contains a functional $tet^R$ gene promoter composed of *S. venezuelae* DNA at its proximal end and pBR322 DNA making up the remainder of the gene. The DNA base sequence of the streptomycete portion of the promoter was established. The promoter region is very rich in G-C base pairs. No potential RNA polymerase attachment sites (Pribnow boxes) and no translational initiation and termination codons are present. In addition to the 3' terminal Alu I site at the streptomycete-pBR322 junction the sequence contains one restriction site each for Hph I, Hpa II and Mbo I as deduced from the DNA base sequence.

pUC1060 is useful as a cloning vector in DNA work wherein desired genes are incorporated into the chimeric plasmid, and the resulting plasmid then transformed into a suitable host.

REFERENCE TO THE DRAWING

Restriction enzyme map for the *S.* sp. 3022a-pBR322 promoter region. The inserted *S.* sp. 3022a segment is located between the Eco R₁ and Hind III, sites.

Following is the DNA sequence of *S.* sp. 3022a-pBR322 promoter region. The *S.* sp. 3022a insert is located upstream from the HindIII site and the *S.* sp. 3022a promoter region is underlined.

cleaved with the same enzyme(s). Upon mixing the linear vector or portions thereof and non-vector DNA's, their single-stranded or blunt ends can pair with each other, and in the presence of a second enzyme known as polynucleotide ligase can be covalently joined to form a single circle of DNA.

The above procedure also can be used to insert a segment of DNA from any plant or animal into pUC1060. For example, the DNA which codes for ribosomal RNA in the frog can be mixed with pUC1060 DNA that has been cleaved. The resulting circular DNA molecules consist of plasmid pUC1060 with an inserted segment of frog rDNA.

The recombinant plasmids containing a desired genetic element, prepared by using pUC1060, can be introduced into a host organism for expression. Examples of valuable genes which can be inserted into host organisms by the above described process are genes coding for somatostatin, rat proinsulin, and proteases.

DETAILED DESCRIPTION OF THE INVENTION

The Microorganisms and Plasmids

The following microorganisms are available from the permanent collection of the Northern Regional Research Laboratory, U.S. Department of Agriculture, Peoria, Illinois, U.S.A.

NRRL B-11371—*E. coli* HB101
NRRL B-12014—*E. coli* RR1 (pBR322)
NRRL B-11441—*S.* sp. 3022a
NRRL B-12376—*E. coli* HB101 (pUC1060)

These deposits are available to the public upon the grant of a patent to the assignee, The Upjohn Company, disclosing them. The deposits are also available as required by foreign patent laws in countries wherein counterparts of the subject application, or its progeny, are filed. However, it should be understood that the availability of a deposit does not constitute a license to practice the subject invention in derogation of patent rights granted by governmental action.

The following examples are illustrative of the process and products of the subject invention but are not to be construed as limiting. All percentages are by weight and all solvent mixture proportions are by volume unless otherwise noted.

EXAMPLE 1—Isolation of Vector pBR322 DNA from *E. coli* NRRL B-b (12014)

A 100 ml. culture of *E. coli* RR1 (pBR322) is grown overnight in L-broth which consists of the following

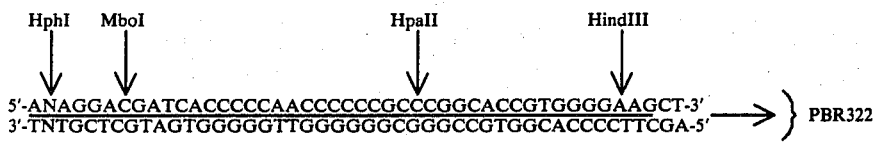

pUC1060 can be used to create recombinant plasmids which can be introduced into host bacteria by transformation. The process of creating recombinant plasmids is well known in the art. Such a process comprises cleaving the isolated vector plasmid, e.g., pUC1060, at specific sites by means of restriction endonucleases, for example, EcoR₁. The plasmid, which is a circular DNA molecule, is thus converted into linear DNA molecules by the enzymes which cut the two DNA strands at a specific site. Other non-vector DNA is similarly ingredients:
Bacto tryptone (Difco)—10 g/liter
Bacto yeast extract (Difco)—5 g/liter
NaCl—5 g/liter
Ampicillin—50 mg/liter The cells are recovered by centrifugation at 17,000×g. for 10 minutes in a refrigerated centrifuge. The pellet is suspended in 2.5 ml. 50 mM tris buffer (pH 8) containing 25% sucrose. One-half ml. of lysozyme stock solution is added (5 mg./ml. in 10 mM Tris.HCl, pH 8). The mixture is allowed to stand in ice for 5 minutes. At this point 1 ml. EDTA (ethylene diamine tetraacetic acid) (0.25 M, pH 8) is added and the mixture is again allowed to stand in ice for 5 minutes. One and a quarter ml. of 5 N NaCl and 1 ml. 10% SDS (sodium dodecyl sulfate) are then added. The mixture is shaken on a Vortex and incubated at 37° C. for 20 minutes. Then 10 μl of ribonuclease A (20 mg./ml.) is added and the sample is again incubated at 37° C. for 20 minutes. The mixture is then kept in ice overnight and then centrifuged at 35,000×g. for 30 minutes in a refrigerated centrifuge. 2 ml. of the supernatant solution (lysate) are carefully removed with a pipette. Four and one-half ml. of TES buffer (30 mM tris.HCl, pH 8, 5 mM EDTA.-$Na_2$, 50 mM NaCl) are mixed with 1.5 ml. EtBr (ethidium bromide) stock (1 mg./ml. in TES buffer) and 7.5 g. solid CsCl. After the salt has dissolved, 2 ml. of the lysate, described above, is added and the mixture is transferred into a polyallomer tube fitting a titanium 50 (Ti 50) head (Beckman ultracentrifuge). The tubes are filled to the top with mineral oil and centrifuged in a Beckman ultracentrifuge at 40,000 rpm in a Ti 50 head at 20° C. for at least 2 days. The DNA is located under a long wave UV-lamp and the heavier band containing the plasmid DNA is removed with a syringe by puncturing the tube wall from the side. The samples are extensively dialysed against 100 volumes of TES buffer at 4° C. Following dialysis 1/10 sample volume of a 3 M Na.Acetate stock solution is added and the plasmid DNA is precipitated by the addition of 2 volumes of cold ethanol. The resulting pellet is then lyophilized and redissolved in 200 μl 10 mM tris buffer, pH 7.8 containing 1 mM EDTA.$Na_2$ and frozen for storage.

EXAMPLE 2—Isolation of Chromosomal DNA from S. sp. 3022a NRRL B-11441

By substituting S. sp. 3022a, NRRL B-11441, for E. coli NRRL B-12014 in Example 1, there is obtained DNA from S. sp. 3022a.

EXAMPLE 3—Preparation of Hybrid Plasmid pUC1060 and Transformation Into Host—NRRL B-12376.

Plasmid pBR322 DNA is digested with $EcoR_1$ and HindIII restriction enzymes by mixing 4 μl of DNA (0.3 μg/μl), 11 μl DD.$H_2O$ (double distilled water), 2 μl 10x high salt restriction buffer (Post, L. E., Arfsten, A. E., Reusser, F. and Nomura, M. 1978. DNA sequences of promoter regions for the str and spc ribosomal protein operons in E. coli. Cell 15, 215–229) and 1.5 μl each of $EcoR_1$ and of HindIII solutions. This mixture is incubated at 37° C. for 1 hr. Five μl of bacterial alkaline phosphatase (BAP.F, Worthington) is then added and the mixture is incubated at 65° C. for 10 minutes. Following the nuclease treatment, 350 μl of 10 mM Tris.-acetate, pH 7.8, and 40 μl of 3M Na.acetate stock solution are added. The sample is extracted three times with an equal volume of phenol, precipitated with ethanol, lyophilized and redissolved in 10 μl 10 mM tris buffer. This solution is used for the ligation reaction described below.

S. sp. 3022a DNA is subjected to Eco $R_1$ and HindIII digestion in a reaction mixture containing 10 μl S. sp. 3022a DNA (0.5 μg/μl), 6 μl DD.$H_2O$, 2 μl 10x high salt restriction buffer and 2 μl each of Eco $R_1$ and HindIII solution. This mixture is kept at 37° C. for 1 hour. The reaction is stopped by incubating the sample at 65° C. for 10 minutes. The solution is then used for the ligation reaction.

For ligation 10 μl pBR322 digestion mix, 20 μl S. sp. 3022a digestion mix, and 30 μl DD.$H_2O$ are combined. Ten μl 0.5 M Tris.HCl, pH 7.8, 20 μl 100 mM DDT (dithiothreitol), 10 μl 100 mM $MgCl_2$, and 10 μl 10 mM ATP (adenosine triphosphate) are mixed separately and then combined with the digested DNA mixture. Finally 1.5 u of $T_4$ ligase is added and the sample is kept in ice for 1–2 days. Following ligation, the solution is adjusted to 0.3 M with Na.acetate and the DNA precipitated with ethanol. The pellet is washed with ethanol and lyophilized. The essentially pure hybrid plasmid pUC1031, thus obtained, is redissolved in 200 μl transformation buffer containing 10 mM Tris.HCl, pH 7, 10 mM $CaCl_2$ and 10 mM $MgCl_2$.

For transformation into E. coli HB101, seed is grown overnight in L-broth and diluted 1:100 into fresh L-broth the next day. The cells are incubated at 37° C. and allowed to grow to an $OD_{600}$ of 0.6. At this point 50 ml. of culture is centrifuged in the cold, the pellet resuspended in 25 ml. cold 10 mM $MgSO_4$ and centrifuged again. The pellet is then resuspended in 25 ml. cold 50 mM $CaCl_2$ solution and kept on ice for 20 minutes. After centrifugation the cells are resuspended in 5 ml. cold 50 mM $CaCl_2$ solution. One hundred μl of ligase mixture (see above) is mixed with 200 μl cell suspension. This mixture is kept in ice for 15 minutes, heated to 42° C. for 2 minutes and then left at room temperature for 10 minutes. Ten μl aliquots are plated on freshly prepared agar plates containing 25 ml. of L-broth, 1.5% agar and 50 μg of ampicillin/ml. Colonies are selected and scored for tetracycline resistance.

Colonies are screened for the presence of plasmids of different sizes by making a small amount of cleared lysate. Single colonies are grown in small cultures overnight. A 1 ml. culture is centrifuged for 2 minutes in an Eppendorf microcentrifuge. The pellet is resuspended in 25 μl 25% sucrose in 50 mM Tris.HCl, pH 8.0. Five μl of a lysozyme solution (5 mg./ml. in 10 mM Tris.HCl, pH 8.0) is added. After 5 minutes at 0° C., 10 μl 0.25 M EDTA, pH 8.0 is added. After an additional 5 minutes incubation at 0° C., 12.5 μl 5 M NaCl and 5 μl 10% SDS are added, and the mixture is quickly shaken by a Vortex mixer. After 1–2 hours at 0° C., the mixture is centrifuged 5 minutes in an Eppendorf microcentrifuge and 20 μl supernatant is analyzed using agarose slab gel electrophoresis. Detection of plasmid DNA and estimation of its approximate size are made by examining gels stained with ethidium bromide under a long-wave ultraviolet lamp.

Suspected transformants are then grown in 10 ml. cultures. Cleared lysates are prepared as described above. The supernatants are treated with pancreatic RNase A (25 mg./ml., 30 minutes at room temperature), and then extracted with phenol. DNA is precipitated from the aqueous phase by ethanol, and then digested with suitable restriction enzymes to analyze DNA fragments cloned in the transformants.

Restriction Endonuclease Digestion and Agarose Gel Electrophoresis

Restriction endonucleases were obtained as commercial preparations from New England Biolabs. Enzyme digestions were carried out as specified in the publication of Post, L. E., Arfsten, A. E., Reusser, F. and Nomura, M., supra.

The digested samples were applied to 1% agarose gels and were electrophoresed for ~3 hours at a constant applied cross voltage of 40 volts. [Shinnick, T. M., Lund, E., Smithies, O. and Blattner, F. R., 1975. Hybridization of labeled RNA and DNA in agarose gels. Nucl. Acids Res. 2, 1911-1929.] The molecular weights of restriction fragments were determined relative to the standard migration patterns of bacteriophage lambda DNA digested with enzyme HindIII [Murray, K. and Murray, N. E. 1975. Phage lambda receptor chromosomes for DNA fragments made with restriction endonuclease III of *Haemophilus influenzae* and restriction endonuclease I of *Escherichia coli.* J. Mol. Biol. 98, 551-564].

Examples of other vectors which can be used in the invention as a substitute for pBR322 are pBR313, which codes for ampicillin and tetracycline resistance, pSC101, which codes for tetracycline resistance.

Examples of other hosts for the vectors are any *E. coli* K-12 derivative [Bacteriological Reviews, Dec. 1972, pages 525-557] (these have been approved by the NIH Guidelines) and yeasts, other fungi, or other bacteria. It is recognized that these latter hosts would also have to be approved by the NIH Guidelines.

Plasmid pUC1060 can be isolated from *E. coli* HB101 transformants by well known procedures, e.g. using the procedure described in Example 1.

DNA base sequence analysis was carried out as described by Maxam and Gilbert (Maxam, A. M. and Gilbert, W. 1977, A New Method for Sequencing DNA. Proc. Natl. Acad. Sci. USA 74, 560-564.

The work described herein was all done in conformity with physical and biological containment requirements specified in the NIH Guidelines.

I claim:

1. *E. coli* HB101 (pUC1060) having the deposit accession number NRRL B-12376.

2. Hybrid plasmid pUC1060 characterized as follows:
(a) it is a hybrid plasmid which has the entire nucleotide sequence of plasmid pBR322 and a foreign DNA insert between the Eco R$_1$ and HindIII sites of pBR322;
(b) said DNA insert is located upstream from the HindIII site of pBR322;
(c) said DNA insert restriction enzyme map is shown in the drawing; and
(d) said DNA insert nucleotide sequence and restriction enzyme sites are as follows:

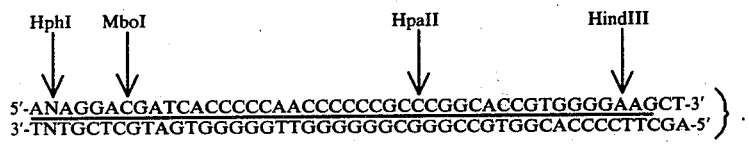

3. A process for preparing hybrid plasmid pUC1060 which comprises:
(a) linearizing plasmid pBR322 with EcoR, and HindIII to obtain linear plasmid DNA;
(b) obtaining chromosomal DNA from *Streptomyces* sp. 3022a NRRL B-11441.
(c) digesting said chromosomal DNA; with Eco R$_1$ and HindIII and
(d) ligating said digested linear plasmid DNA from pBR322 and said digested chromosomal DNA from *Streptomyces* sp. 3022a NRRL B-11441, to obtain hybrid plasmid pUC1060.

4. A process for cloning plasmid pUC1060 into a suitable host by transformation wherein said suitable host is grown in an aqueous nutrient medium, isolated from the medium and suspended in a CaCl$_2$ solution, and mixed with ligase mixture containing plasmid pUC1060.

5. A process, according to claim 4, wherein said suitable host is a bacterium.

6. A process, according to claim 5, wherein said bacterium is *E. coli* HB101.

* * * * *